(12) United States Patent
Otani

(10) Patent No.: US 12,102,292 B2
(45) Date of Patent: Oct. 1, 2024

(54) ENDOSCOPE SYSTEM

(71) Applicant: FUJIFILM Corporation, Tokyo (JP)

(72) Inventor: Kenichi Otani, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 430 days.

(21) Appl. No.: 17/496,197

(22) Filed: Oct. 7, 2021

(65) Prior Publication Data
US 2022/0022738 A1 Jan. 27, 2022

Related U.S. Application Data

(63) Continuation of application No. PCT/JP2020/014068, filed on Mar. 27, 2020.

(30) Foreign Application Priority Data

Apr. 10, 2019 (JP) .................. 2019-074672

(51) Int. Cl.
A61B 1/00 (2006.01)
A61B 1/05 (2006.01)
A61B 1/06 (2006.01)

(52) U.S. Cl.
CPC ...... A61B 1/00186 (2013.01); A61B 1/00009 (2013.01); A61B 1/05 (2013.01); A61B 1/0638 (2013.01)

(58) Field of Classification Search
CPC ... A61B 1/00186; A61B 1/00009; A61B 1/05; A61B 1/0638; A61B 1/0646; A61B 1/0653; A61B 1/0655; A61B 2018/2272
USPC ....................................... 600/160
See application file for complete search history.

(56) References Cited

U.S. PATENT DOCUMENTS

| | | | |
|---|---|---|---|
| 7,179,222 B2 | 2/2007 | Imaizumi et al. | |
| 2017/0135555 A1 | 5/2017 | Yoshizaki | |
| 2017/0172403 A1* | 6/2017 | Fink | A61B 1/0684 |
| 2019/0008361 A1* | 1/2019 | Imai | G06T 5/73 |
| 2019/0110671 A1* | 4/2019 | Daidoji | F21S 2/00 |
| 2019/0387964 A1 | 12/2019 | Kobayashi | |

(Continued)

FOREIGN PATENT DOCUMENTS

| | | |
|---|---|---|
| CN | 107126184 A | 9/2017 |
| CN | 107174189 A | 9/2017 |

(Continued)

OTHER PUBLICATIONS

US 6,692,429 B1, 02/2004, Imaizumi et al. (withdrawn)

(Continued)

Primary Examiner — Timothy J Neal
Assistant Examiner — James Edward Boice
(74) Attorney, Agent, or Firm — Studebaker & Brackett PC

(57) ABSTRACT

The endoscope system includes a light source device that illuminates a subject, dichroic mirrors that separate a reflected light beam from the subject into a first blue light beam, a second blue light beam, a green light beam, and a red light beam, a CMOS sensor that picks up an image of the first blue light beam, a CMOS sensor that picks up an image of the second blue light beam, a CMOS sensor that picks up an image of the green light beam, and a CMOS sensor that picks up an image of the red light beam, and a control unit that controls image pickup. The control unit independently controls the exposure times of the CMOS sensors.

11 Claims, 17 Drawing Sheets

(56) References Cited

U.S. PATENT DOCUMENTS

| | | | |
|---|---|---|---|
| 2020/0058131 A1 | 2/2020 | Takahashi | |
| 2020/0196845 A1* | 6/2020 | Ikai | A61B 1/041 |
| 2021/0338039 A1* | 11/2021 | Koizumi | A61B 1/000094 |

FOREIGN PATENT DOCUMENTS

| | | |
|---|---|---|
| EP | 3430969 A1 | 1/2019 |
| EP | 3586716 A1 | 1/2020 |
| JP | 2009-039561 A | 2/2009 |
| JP | 2018-023612 A | 2/2018 |
| JP | 2018-166986 A | 11/2018 |
| WO | 2017/085793 A1 | 5/2017 |
| WO | 2017/159059 A1 | 9/2017 |
| WO | 2018/163500 A1 | 9/2018 |
| WO | 2018/198251 A1 | 11/2018 |

OTHER PUBLICATIONS

International Search Report issued in PCT/JP2020/014068; mailed Jun. 16, 2020.

International Preliminary Report On Patentability and Written Opinion issued in PCT/JP2020/014068; issued Sep. 28, 2021.

Communication pursuant to Article 94(3) EPC issued by the European Patent Office on Sep. 6, 2023, which Corresponds to European Patent Application No. 20787366.2-1126 and is related to U.S. Appl. No. 17/496,197.

An Office Action; "Notice of Reasons for Refusal", mailed by the Japanese Patent Office on May 10, 2022, which corresponds to Japanese Patent Application No. 2021-513567 and is related to U.S. Appl. No. 17/496,197 with English language translation.

An Office Action mailed by China National Intellectual Property Administration on Nov. 13, 2023, which corresponds to Chinese Patent Application No. 202080027664.0 and is related to U.S. Appl. No. 17/496,197; with English language translation.

The extended European search report issued by the European Patent Office on May 6, 2022, which corresponds to European Patent Application No. 20787366.2-1126 and is related to U.S. Appl. No. 17/496,197.

An Office Action mailed by the Chinese Patent Office on May 21, 2024, which corresponds to Chinese Patent Application No. 202080027664.0 and is related to U.S. Appl. No. 17/496,197.

* cited by examiner

ENDOSCOPE SYSTEM

CROSS-REFERENCE TO RELATED APPLICATIONS

This application is a Continuation of PCT International Application No. PCT/JP2020/014068 filed on 27 Mar. 2020, which claims priority under 35 U.S.C § 119(a) to Japanese Patent Application No. 2019-074672 filed on 10 Apr. 2019. The above application is hereby expressly incorporated by reference, in its entirety, into the present application.

BACKGROUND OF THE INVENTION

1. Field of the Invention

The present invention relates to an endoscope system.

2. Description of the Related Art

In the medical field, an endoscope system comprising a light source device, an endoscope, and a processor device has become widespread. In the endoscope system, an illumination light beam is emitted and a subject is illuminated with the illumination light beam, and an image of a reflected light beam from the subject is picked up and displayed on a monitor or the like. Further, in recent years, as described in WO2017/085793A1 (corresponding to US2017/135555A1), an endoscope system that not only picks up and observes an image of the appearance of the subject, but also calculates biological information, such as oxygen saturation, using the image obtained by the image pickup of the subject, has been known. An arithmetic operation or the like is performed, by using the image obtained by the image pickup of the subject with an illumination light beam including a light beam in a wavelength range in which the light absorption coefficient is changed according to the oxygen saturation of hemoglobin, so that the oxygen saturation is calculated.

SUMMARY OF THE INVENTION

However, there is a problem that it is difficult to acquire biological information with high accuracy in a case where the wavelength ranges specialized for acquiring the biological information are close to each other.

The present invention has been made in view of the above background, and an object thereof is to provide an endoscope system capable of acquiring biological information with higher accuracy.

There is provided an endoscope system according to an aspect of the present invention that illuminates a subject and picks up an image of a reflected light beam from the subject, the endoscope system comprising: a spectral element that separates the reflected light beam into light beams in a plurality of wavelength ranges; a plurality of image pickup elements on which the light beams in the plurality of wavelength ranges, which are separated by the spectral element, are incident, respectively; and an image pickup control unit that controls exposure times of the plurality of image pickup elements for each image pickup element to perform image pickup.

The image pickup elements may include a first image pickup element on which a light beam in a first wavelength range including a first wavelength is incident, and a second image pickup element on which a light beam in a second wavelength range including a second wavelength of which a wavelength difference from the first wavelength is 30 nm or less is incident, and the exposure time of at least one of the first image pickup element or the second image pickup element may be longer than the exposure time of the other image pickup element.

A first blue light beam as the light beam in the first wavelength range may be incident on the first image pickup element, and a first blue image may be picked up by the first image pickup element, and a second blue light beam as the light beam in the second wavelength range may be incident on the second image pickup element, and a second blue image may be picked up by the second image pickup element.

The first wavelength may be 445 nm and the second wavelength may be 473 nm.

An oxygen saturation calculation unit that calculates oxygen saturation using the first blue image and the second blue image may further be provided.

A first red light beam as the light beam in the first wavelength range may be incident on the first image pickup element, and a first red image may be picked up by the first image pickup element, and a second red light beam as the light beam in the second wavelength range may be incident on the second image pickup element, and a second red image may be picked up by the second image pickup element.

The first wavelength may be 600 nm and the second wavelength may be 630 nm.

A biological information calculation unit that calculates biological information using the first red image and the second red image may further be provided.

A first image pickup element and a second image pickup element may be provided as the image pickup elements, the spectral element may separate a light beam in a first wavelength range including a specific wavelength from the reflected light beam, and the light beam in the first wavelength range may be incident on the first image pickup element, and a remaining light beam may be incident on the second image pickup element.

The image pickup control unit may continuously perform image pickup at a common frame rate for all the image pickup elements.

In a case where there is an image pickup element that performs image pickup with an exposure time longer than the frame rate, the image pickup control unit may change the frame rate longer than a longest time of the exposure times for all the image pickup elements.

A notification unit that, in a case where the frame rate is changed, gives notification of the change may be further provided.

With the endoscope system according to the aspect of the present invention, biological information can be acquired with higher accuracy.

DESCRIPTION OF THE PREFERRED EMBODIMENTS

First Embodiment

Figure 1:
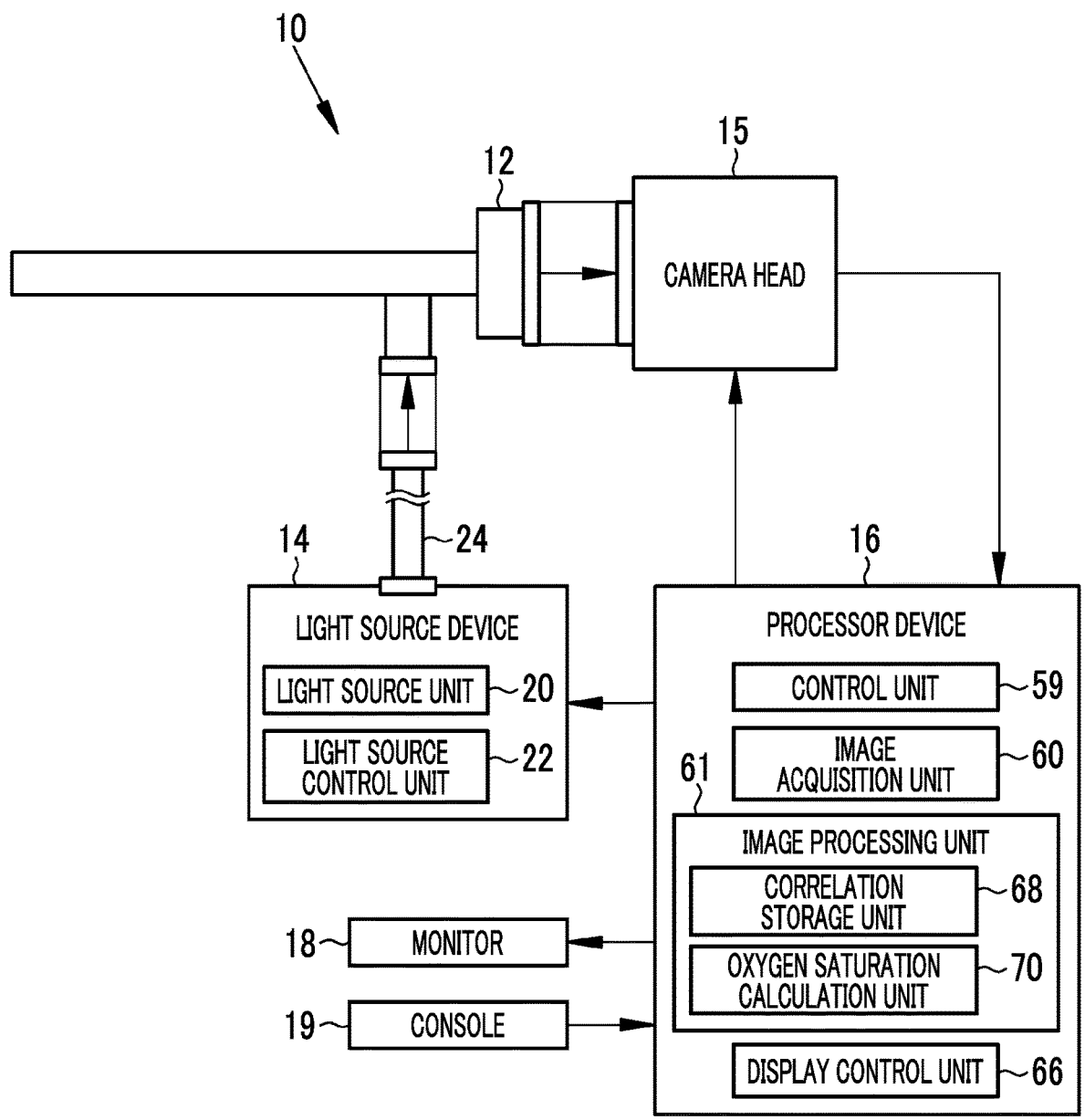
FIG. 1 is a configuration diagram of an endoscope system.

As shown in FIG. 1, an endoscope system 10 comprises an endoscope 12, a light source device 14, a camera head 15, a processor device 16, a monitor 18, and a console 19.

The endoscope 12 is hard and elongated, and is inserted into a subject to be examined. An optical system that is used to form a subject image, and an optical system that is used to irradiate the subject with an illumination light beam are provided inside the endoscope 12. The light source device 14 generates an illumination light beam. The camera head 15 picks up an image of the subject. The processor device 16 performs system control, image processing, and the like of the endoscope system 10. The monitor 18 is a display unit that displays the image picked up by the endoscope 12. The console 19 is an input device which is used to, for example, input settings to the processor device 16 and the like.

The light source device 14 comprises a light source unit 20 that emits an illumination light beam, and a light source control unit 22 that controls the operation of the light source unit 20.

The light source unit 20 emits an illumination light beam with which the subject is illuminated, an excitation light beam that is used to emit the illumination light beam, or the like. The light source unit 20 includes, for example, a light source of a laser diode (hereinafter, referred to as an LD), a light emitting diode (LED), a xenon lamp, or a halogen lamp, and emits at least a white illumination light beam or an excitation light beam that is used to emit the white illumination light beam. The white color includes so-called pseudo white color, which is substantially the same as the white color in the image pickup of the subject using the endoscope 12.

Further, the light source unit 20 includes, as necessary, a phosphor that is irradiated with an excitation light beam to emit a light beam, or an optical filter that adjusts a wavelength range, a spectrum, the amount of light beam, or the like of an illumination light beam or excitation light beam. In addition, the light source unit 20 can emit a light beam having a specific wavelength range, which is necessary for picking up an image that is used to calculate biological information, such as oxygen saturation of hemoglobin contained in the subject.

Figure 2:
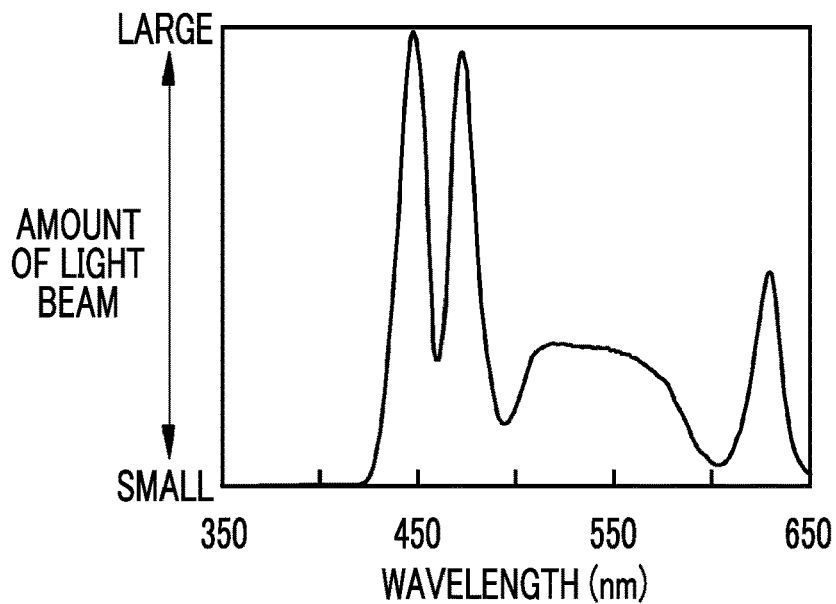
FIG. 2 is a graph showing an emission spectrum of a light source.

FIG. 2 shows the emission spectrum of an illumination light beam emitted by the light source unit 20 of the present embodiment. In the present embodiment, the light source unit 20 includes a first LED that emits a light beam of blue color (first blue light beam) having a central wavelength of about 445 nm (first wavelength), and a second LED that emits a light beam of blue color (second blue light beam) having a central wavelength of about 473 nm (second wavelength). Further, the light source unit 20 includes a third LED that emits a light beam of green color (green light beam) having a central wavelength of about 540 nm, and a fourth LED that emits a light beam of red color (red light beam) having a central wavelength of about 650 nm.

Figure 3:
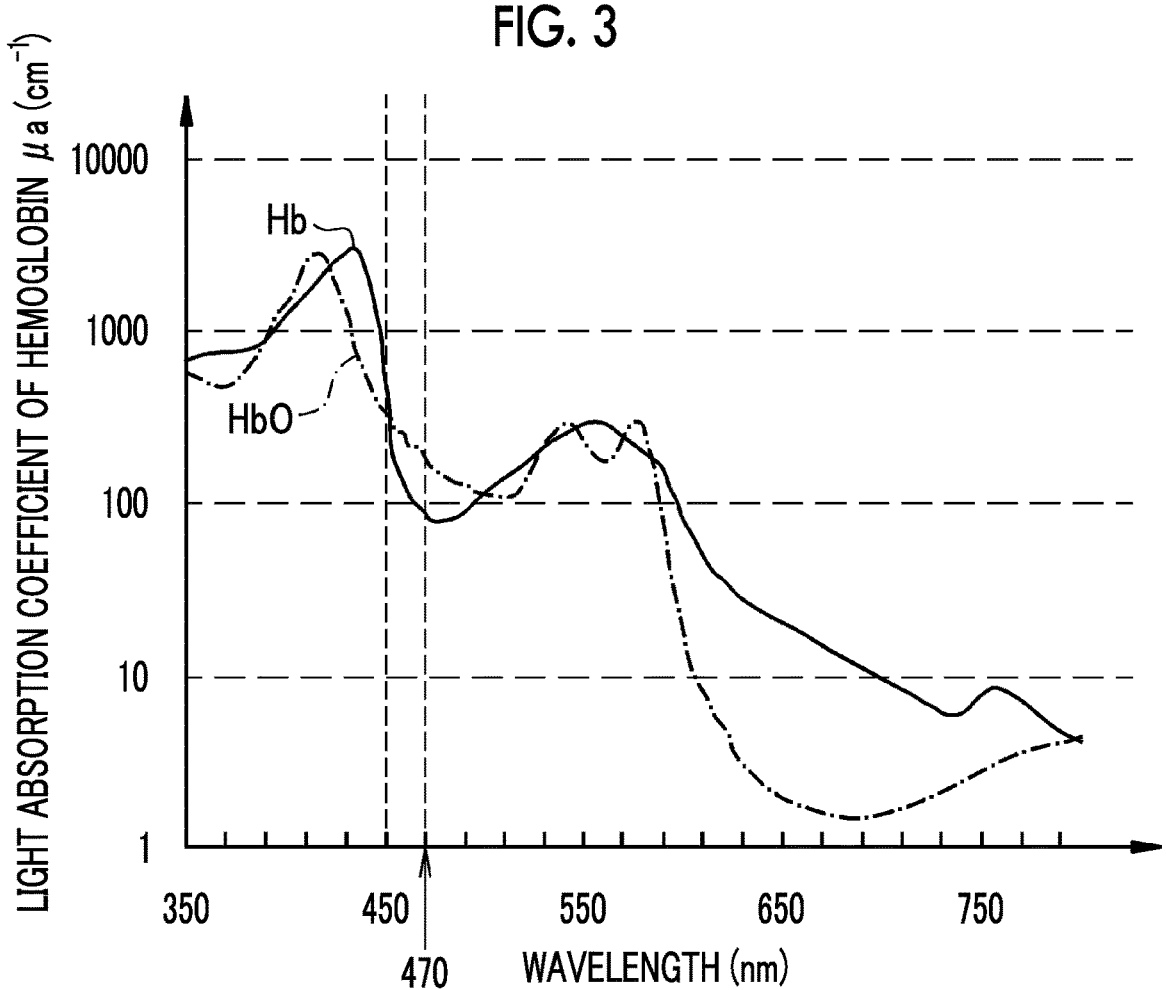
FIG. 3 is a graph showing light absorption coefficients of hemoglobin and oxidized hemoglobin.

Here, the first blue light beam and the second blue light beam are light beams having specific wavelength ranges, which are necessary for picking up an image that is used to calculate biological information, such as oxygen saturation of hemoglobin contained in the subject. That is, as shown in FIG. 3, a wavelength of about 445 nm which is a central wavelength of the first blue light beam is a wavelength at which the light absorption coefficients of oxidized hemoglobin and reduced hemoglobin hardly differ from each other. A wavelength of about 473 nm which is a central wavelength of the second blue light beam is a wavelength at which the difference between the light absorption coefficients of oxidized hemoglobin (HbO) and reduced hemoglobin (Hb) is approximately maximized. Accordingly, the subject is irradiated with an illumination light beam including the first blue light beam and the second blue light beam, the image thereof is picked up, and the light absorption coefficients of the first blue light beam and the second blue light beam are obtained from the picked-up image, so that biological information, such as oxygen saturation of hemoglobin contained in the subject, can be calculated.

Returning to FIG. 1, the light source control unit 22 controls the on or off, the amount of light beam emitted of each light source constituting the light source unit 20. The illumination light beam emitted by the light source unit 20 is incident on the endoscope 12 via a light guide 24, is guided to the distal end of the endoscope 12 via the optical system (optical system that is used to irradiate the subject with an illumination light beam) built in the endoscope 12, and is emitted from the distal end of the endoscope 12 toward the subject. After that, the illumination light beam is reflected by the subject, and the reflected light beam from the subject is guided to the camera head 15 via the optical system (optical system that is used to form a subject image) built in the endoscope 12.

Figure 4:
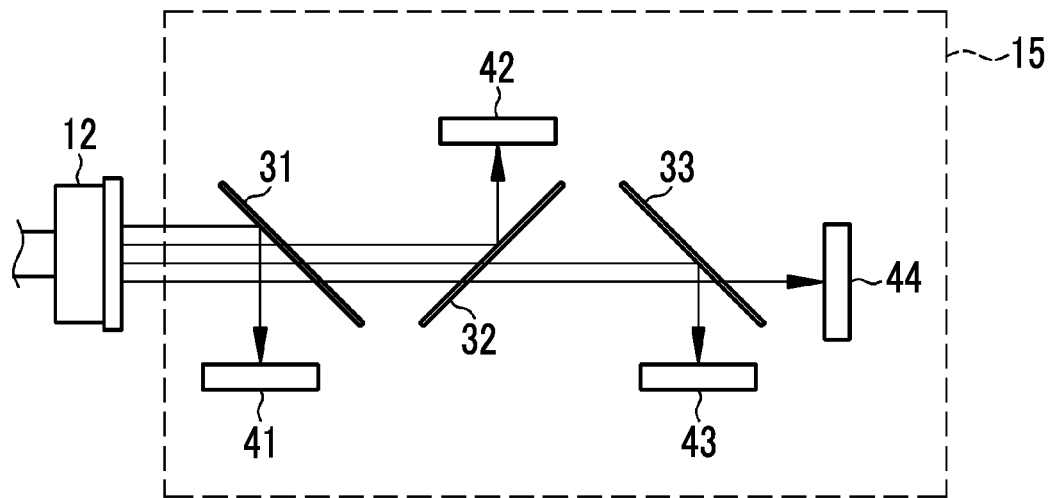
FIG. 4 is a configuration diagram of a camera head.

As shown in FIG. 4, the camera head 15 comprises dichroic mirrors (spectral elements) 31, 32, and 33, and a complementary metal oxide semiconductor (CMOS) sensors (image pickup elements) 41, 42, 43, and 44.

The dichroic mirrors 31, 32, and 33 are provided so as to separate the reflected light beam from the subject illuminated with the illumination light beam, into light beams in a plurality of wavelength ranges. In the present embodiment, the dichroic mirrors 31, 32, and 33 separate the reflected light beam from the subject into four light beams of a first blue light beam, which is a light beam in a wavelength range (first wavelength range) including a wavelength of 445 nm (first wavelength), a second blue light beam, which is a light beam in a wavelength range (second wavelength range) including a wavelength of 473 nm (second wavelength), a green light beam, and a red light beam.

Specifically, the dichroic mirrors 31, 32, and 33 are arranged in this order from the subject side, and the reflected light beam (first blue light beam, second blue light beam, green light beam, and red light beam) from the subject is first separated into the first blue light beam and the other light beams (second blue light beam, green light beam, and red light beam) by the dichroic mirror 31 by which the first blue light beam is reflected. The second blue light beam, the green light beam, and the red light beam passed through the dichroic mirror 31 are separated into the second blue light beam and the other light beams (green light beam and red light beam) by the dichroic mirror 32 by which the second blue light beam is reflected. The green light beam and the red light beam passed through the dichroic mirror 32 are separated into the green light beam and the red light beam by the dichroic mirror 33 by which the green light beam is reflected and through which the red light beam is passed.

Figure 5:
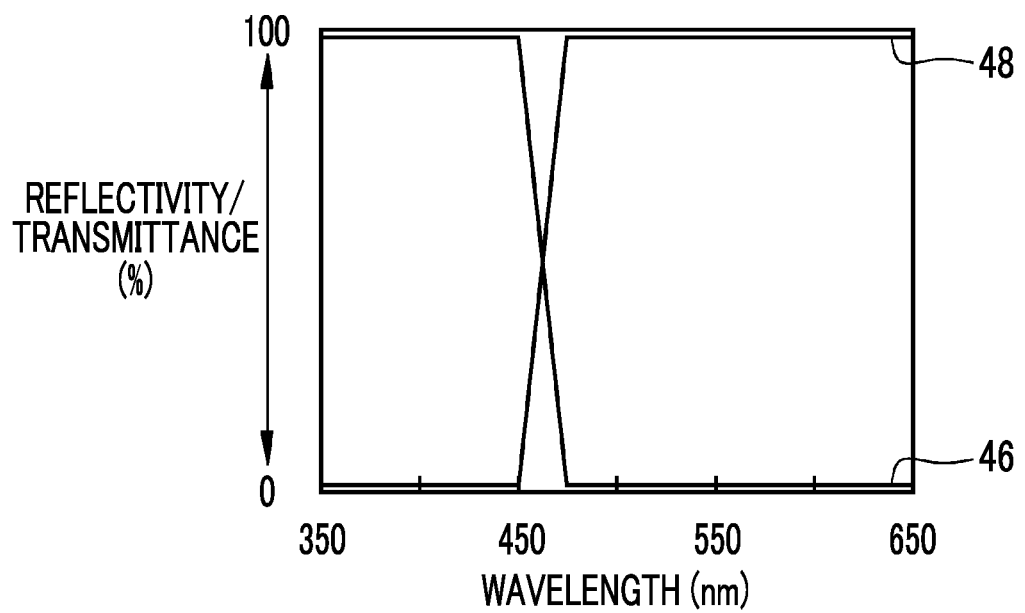
FIG. 5 is a characteristic diagram of a dichroic mirror.

As shown in FIG. 5, in the present embodiment, a dichroic mirror having features that the reflectivity and the transmittance at a wavelength of 449 nm are 100% and 0%, respectively, the reflectivity and the transmittance at a wavelength of 474 nm are 0% and 100%, respectively, and in a wavelength range of 449 nm to 474 nm, the reflectivity decreases in inverse proportion to the wavelength and the transmittance increases in proportion to the wavelength, is used as the dichroic mirror 31. That is, in the present embodiment, in the reflected light beam from the subject, a light beam having a wavelength of less than 474 nm is the first blue light beam (see FIG. 8). In FIG. 5, and FIGS. 6, 7, 23, and 25, which will be described later, a reference numeral 46 is given to a line showing the relationship between the wavelength and the reflectivity of the light beam to be reflected, and a reference numeral 48 is given to a line showing the relationship between the wavelength and the transmittance of the light beam to be transmitted.

Figure 6:
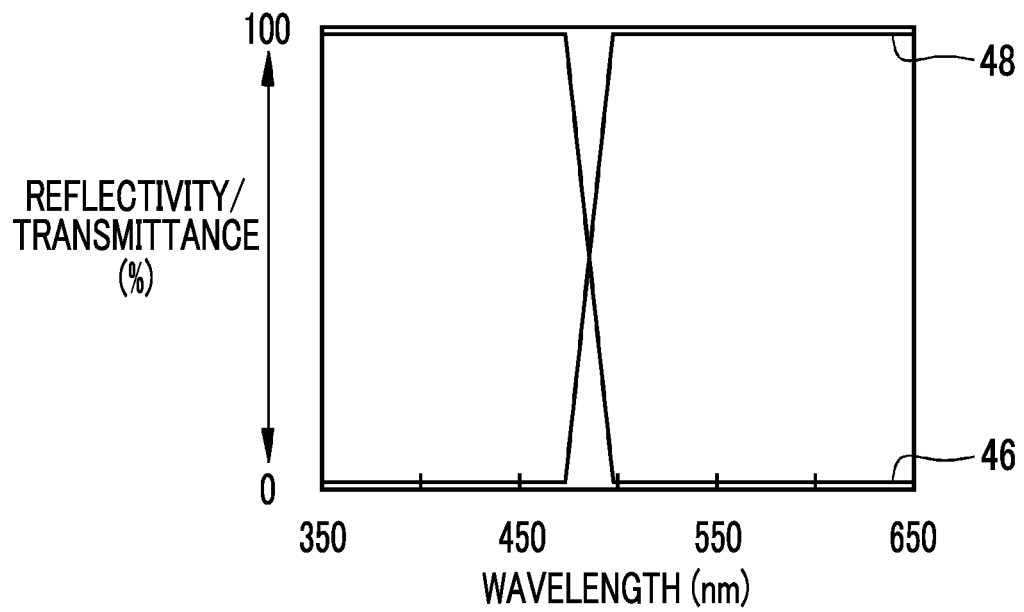
FIG. 6 is a characteristic diagram of another dichroic mirror.

Further, as shown in FIG. 6, in the present embodiment, a dichroic mirror having features that the reflectivity and the transmittance at a wavelength of 472 nm are 100% and 0%, respectively, the reflectivity and the transmittance at a wavelength of 497 nm are 0% and 100%, respectively, and in a wavelength range of 472 nm to 497 nm, the reflectivity decreases in inverse proportion to the wavelength and the transmittance increases in proportion to the wavelength, is used as the dichroic mirror 32. That is, in the present embodiment, in the reflected light beam from the subject, a light beam having a wavelength of more than 449 nm and less than 497 nm is the second blue light beam (see FIG. 9).

Figure 7:
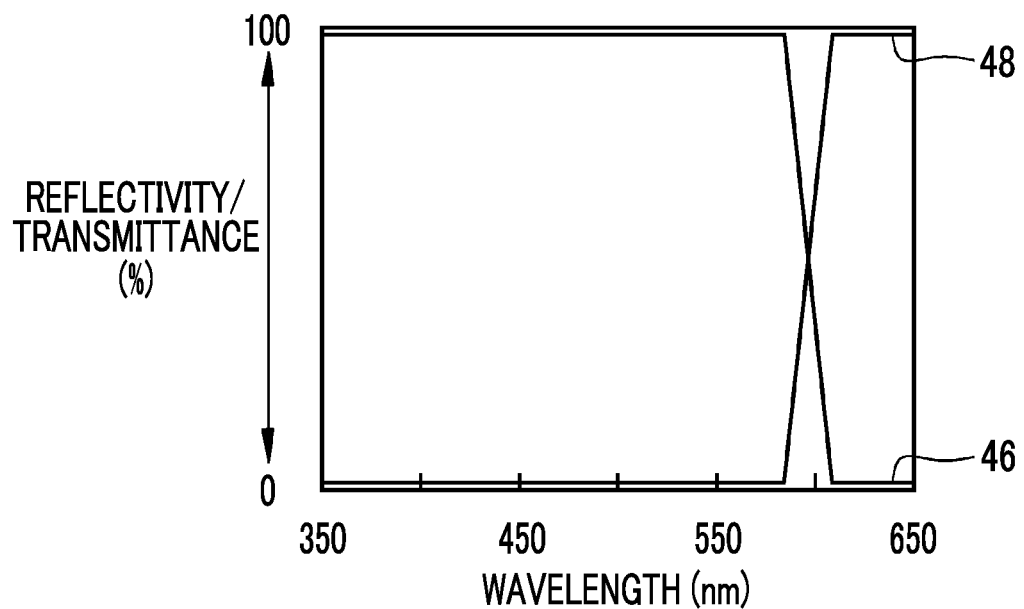
FIG. 7 is a characteristic diagram of still another dichroic mirror.

Furthermore, as shown in FIG. 7, in the present embodiment, a dichroic mirror having features that the reflectivity and the transmittance at a wavelength of 583 nm are 100% and 0%, respectively, the reflectivity and the transmittance at a wavelength of 608 nm are 0% and 100%, respectively, and in a wavelength range of 583 nm to 608 nm, the reflectivity decreases in inverse proportion to the wavelength and the transmittance increases in proportion to the wavelength, is used as the dichroic mirror 33. That is, in the present embodiment, in the reflected light beam from the subject, a light beam having a wavelength of more than 473 nm and less than 608 nm is the green light beam (see FIG. 10). Further, in the present embodiment, in the reflected light beam from the subject, a light beam having a wavelength of more than 583 nm is the red light beam (see FIG. 11).

The CMOS sensors 41, 42, 43, and 44 are provided so as to perform image pickup of the subject. In the present embodiment, the first blue light beam reflected by the dichroic mirror 31 is incident on the CMOS sensor 41 and the image thereof is picked up, the second blue light beam reflected by the dichroic mirror 32 is incident on the CMOS sensor 42 and the image thereof is picked up, the green light beam reflected by the dichroic mirror 33 is incident on the CMOS sensor 43 and the image thereof is picked up, and the red light beam passed through all the dichroic mirrors 31, 32, 33 is incident on the CMOS sensor 44 and the image thereof is picked up. As the image pickup element, an image pickup element other than the CMOS sensor, such as a charge coupled device (CCD) sensor, may be used instead of the CMOS sensor.

Figure 8:
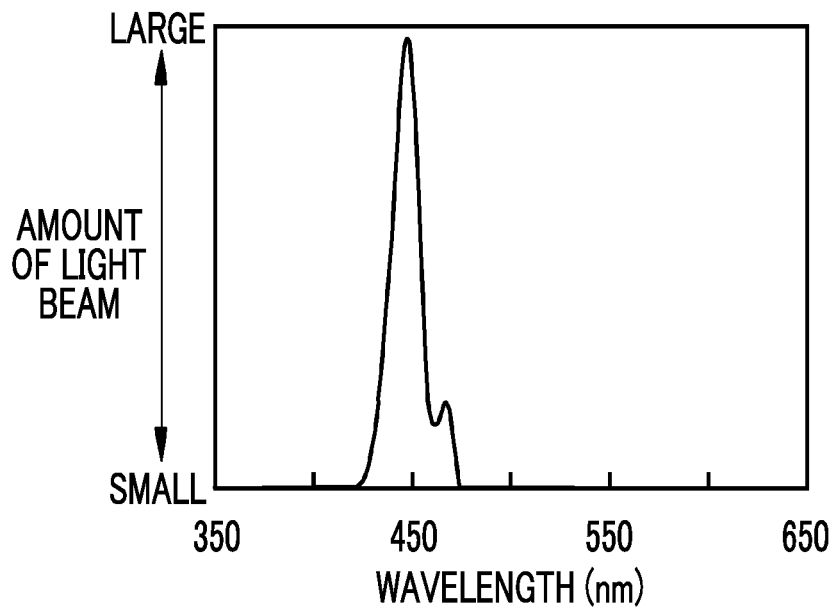
FIG. 8 is a graph showing a spectrum of a first blue light beam.
Figure 9:
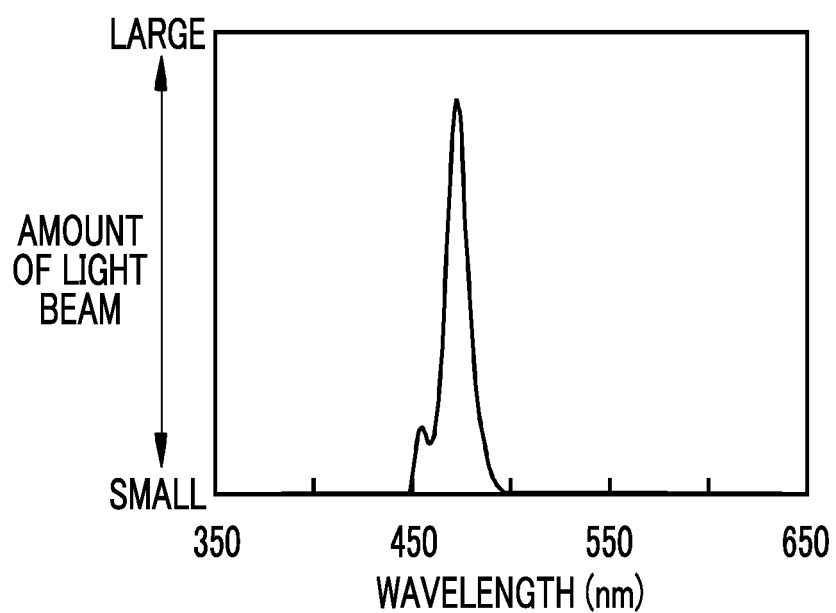
FIG. 9 is a graph showing a spectrum of a second blue light beam.
Figure 10:
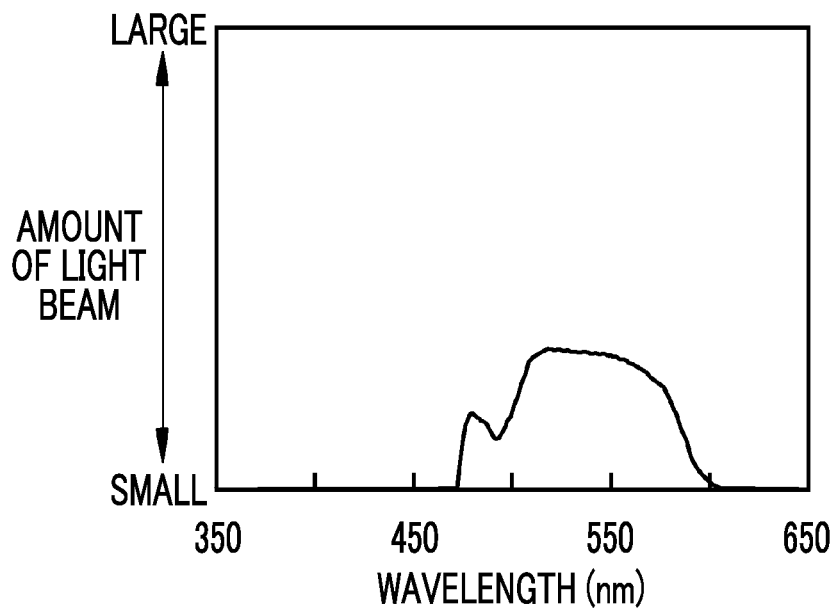
FIG. 10 is a graph showing a spectrum of a green light beam.
Figure 11:
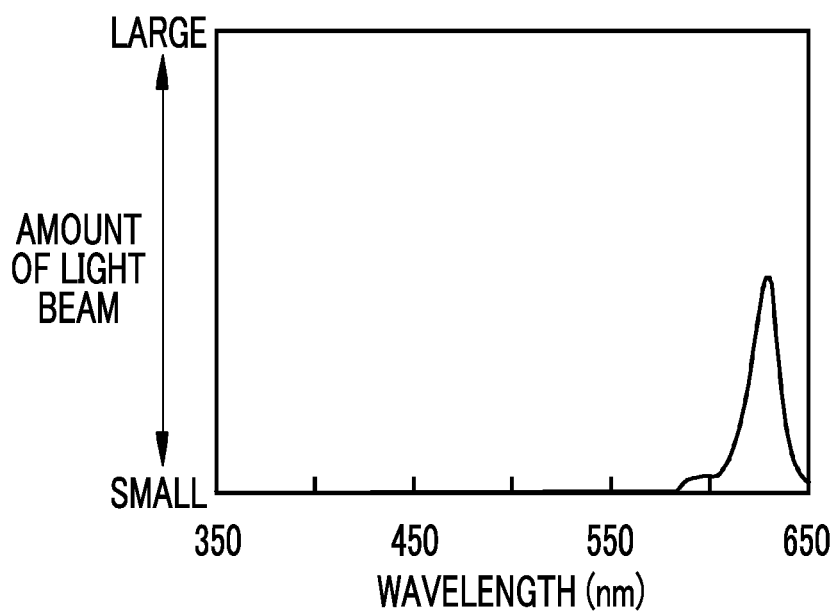
FIG. 11 is a graph showing a spectrum of a red light beam.

The features of the dichroic mirrors 31, 32, and 33 are as described above (see FIGS. 5 to 7). Therefore, in a case where the spectrum of the reflected light beam from the subject is the spectrum shown in FIG. 2, the spectrum of the first blue light beam incident on the CMOS sensor 41 is as shown in FIG. 8, the spectrum of the second blue light beam incident on the CMOS sensor 42 is as shown in FIG. 9, the spectrum of the green light beam incident on the CMOS sensor 43 is as shown in FIG. 10, and the spectrum of the red light beam incident on the CMOS sensor 44 is as shown in FIG. 11. Although the example of using a dichroic mirror as the spectral element has been described, for example, an optical element other than the dichroic mirror, such as a prism, may be used as the spectral element.

Here, the amount of the second blue light beam (see FIG. 9) incident on the CMOS sensor 42 is smaller than that of the second blue light beam (see FIG. 2) included in the reflected light beam from the subject. This occurs because the first wavelength (445 nm in the present embodiment), which is the central wavelength of the first blue light beam, and the second wavelength (473 nm in the present embodiment), which is the central wavelength of the second blue light beam, are close to each other (the difference is 30 nm or less), and the reflectivity (transmittance) of the dichroic mirror does not have a binary value of 0% and 100% and in the wavelength range of the reflectivity (transmittance) of 0% to 100%, the relationship between the wavelength and the reflectivity (transmittance) is, for example, a proportional (or inversely proportional) relationship (the reflectivity (transmittance) has a value other than 0% or 100%).

Figure 12:
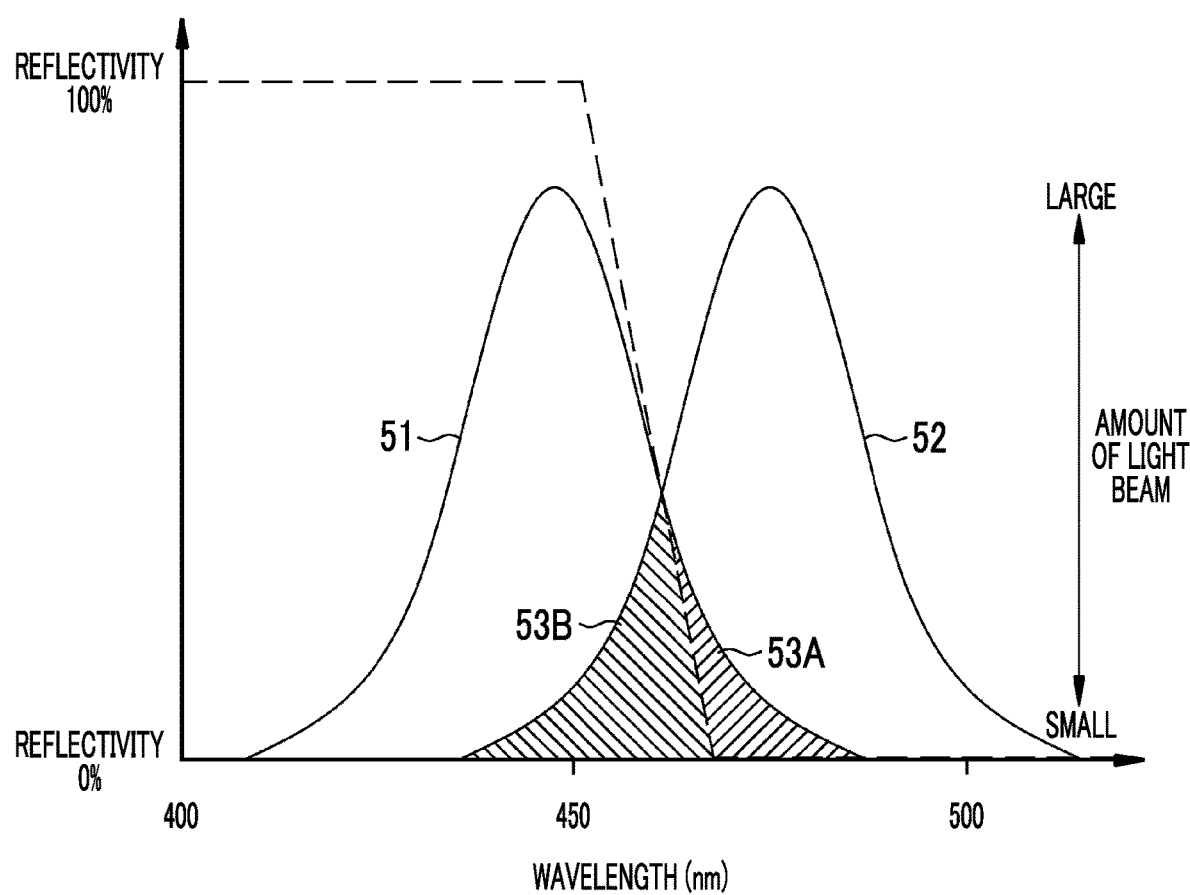
FIG. 12 is an explanatory diagram for illustrating a decrease in the second blue light beam.

Specifically, as shown in FIG. 12, in a case where the reflected light beam from the subject includes a light beam having a central wavelength of 445 nm (light beam having a spectrum with a reference numeral 51) and a light beam having a central wavelength of 473 nm (light beam having a spectrum with reference numeral 52), and as shown by the broken line in the figure, the reflected light beam is separated by a dichroic mirror having features that the reflectivity at a wavelength of 450 nm is 100%, the reflectivity at a wavelength of 470 nm is 0%, and the reflectivity in a wavelength range of 450 nm to 470 nm is inversely proportional to the wavelength, although in a region 53A, the reflected light beam originally should be separated into the first blue light beam, a large amount of the reflected light beam is separated into the second blue light beam. On the contrary, although in a region 53B, the reflected light beam originally should be separated into the second blue light beam, a large amount of the reflected light beam is separated into the first blue light beam. As described above, since the first blue light beam and the second blue light beam cannot be accurately dispersed (separated), the above-described decrease in the amount of light beam occurs.

Returning to FIG. 1, the processor device 16 has a control unit (image pickup control unit) 59, an image acquisition unit 60, an image processing unit 61, and a display control unit 66.

The control unit 59 controls the endoscope system 10, such as illumination control (control of the light source device 14) and imaging control (control of the camera head 15), in an integrated manner. In a case where the input of various settings using the console 19 or the like is received, the control unit 59 makes each unit of the endoscope system 10, such as the light source control unit 22, the camera head 15, and/or the image processing unit 61, receive the input of the setting.

The control unit 59 drives each of the CMOS sensors 41, 42, 43, and 44 of the camera head 15 to continuously pick up the images in a preset image pickup cycle (frame rate). In the present embodiment, the frame rate is 60 frames per second (fps) for all of the CMOS sensors 41, 42, 43, and 44. That is, in the present embodiment, the preset image pickup cycle (frame rate) is 60 fps, and the frame rate is common to all the image pickup elements (all of the CMOS sensors 41, 42, 43, and 44). Accordingly, in the present embodiment, 60 frames (sheets) of images are picked up per second by each of the CMOS sensors 41, 42, 43, and 44.

Figure 13:
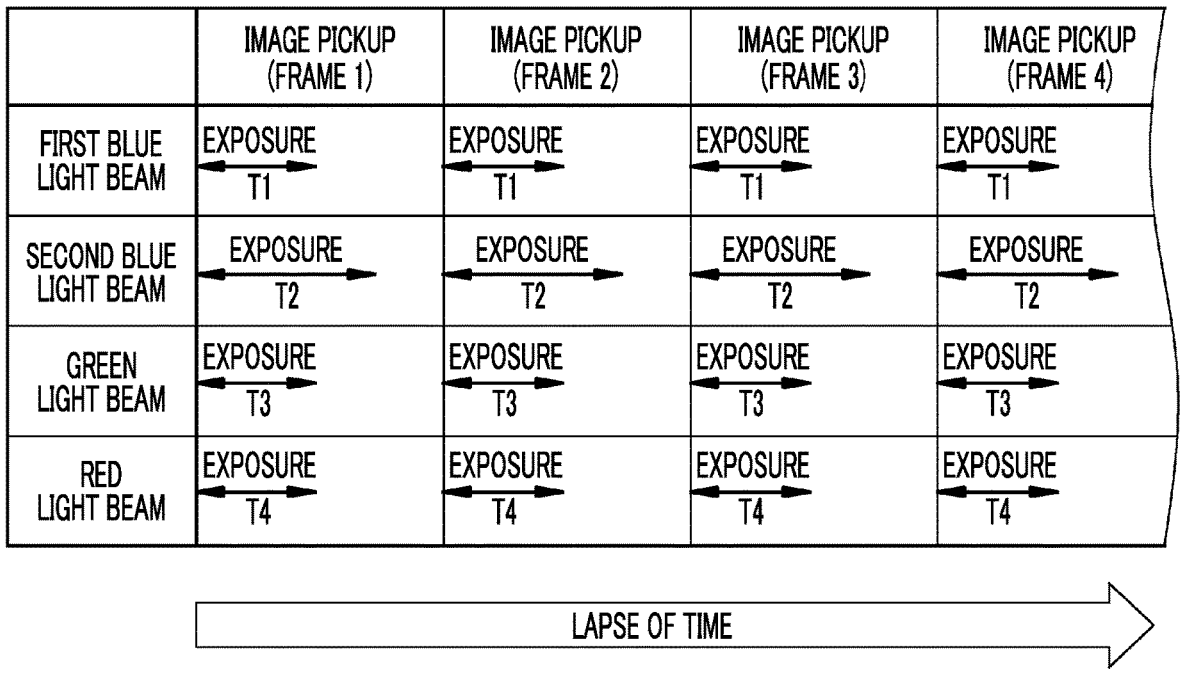
FIG. 13 is an explanatory diagram showing an exposure time of each CMOS sensor.

Further, as shown in FIG. 13, in the image pickup by each of the CMOS sensors 41, 42, 43, and 44, the control unit 59 independently controls the shutter speed of the electronic shutters of the CMOS sensors 41, 42, 43, and 44, that is, the exposure times, for each of the CMOS sensors 41, 42, 43, and 44. As described above, in the present embodiment, the amount of the second blue light beam (see FIG. 9) incident on the CMOS sensor 42 is smaller than that of the second blue light beam (see FIG. 2) included in the reflected light beam from the subject. Therefore, the control unit 59 makes the exposure time T2 of the CMOS sensor 42 longer than each of the exposure times T1, T3, and T4 of the CMOS sensors 41, 43, and 44. As described above, the exposure time of the image pickup element in which the amount of incident light beam decreases is made longer than each of the exposure times of the other image pickup elements to make up for the decrease in the amount of light beam, so that the biological information can be acquired with higher accuracy. Further, for example, in comparison with a case where, in order to make up for the decrease in the amount of light beam, the amplification factor of the signal value of the image picked up by the image pickup element in which the amount of incident light beam decreases is made higher than the amplification factor of the signal value of the image picked up by each of the other image pickup elements, the noise component is not amplified.

The image acquisition unit 60 acquires an image picked up by the CMOS sensor 41 (hereinafter, a first blue image), an image picked up by the CMOS sensor 42 (hereinafter, a second blue image), an image picked up by the CMOS sensor 43 (hereinafter, a green image), and an image picked up by the CMOS sensor 44 (hereinafter, a red image). As a result, the image acquisition unit 60 acquires an image necessary for calculating specific biological information. The specific biological information is oxygen saturation, blood vessel depth, blood vessel density or the like, or other information obtained by an arithmetic operation or the like using the image obtained by the image pickup of the subject. In the present embodiment, the specific biological information is oxygen saturation.

The image processing unit 61 generates an image for display by using the image acquired by the image acquisition unit 60. In the present embodiment, the image processing unit 61 is provided with a correlation storage unit 68 and an oxygen saturation calculation unit 70. The correlation storage unit 68 stores correlation information indicating the correlation between the signal values and/or the ratio of the signal values of the images acquired by the image acquisition unit 60, and the oxygen saturation. The oxygen saturation calculation unit 70 reads out the correlation information from the correlation storage unit 68 and calculates the oxygen saturation by using the correlation information.

Further, the image processing unit 61 generates an image equivalent to an image that is visually recognized in a case where the subject is irradiated with a white light beam, so-called a white image, by using, for example, the first blue image, the second blue image, the green image, and the red image. Then, the image processing unit 61 colors the white image by using an oxygen saturation value calculated by the oxygen saturation calculation unit 70, to generate an oxygen saturation image representing the oxygen saturation value in color, as the image for display.

The display control unit 66 acquires the image for display from the image processing unit 61, converts the acquired image into a format suitable for display, and outputs the image to the monitor 18. As a result, in the present embodiment, the oxygen saturation image is displayed on the monitor 18.

Second Embodiment

Figure 14:
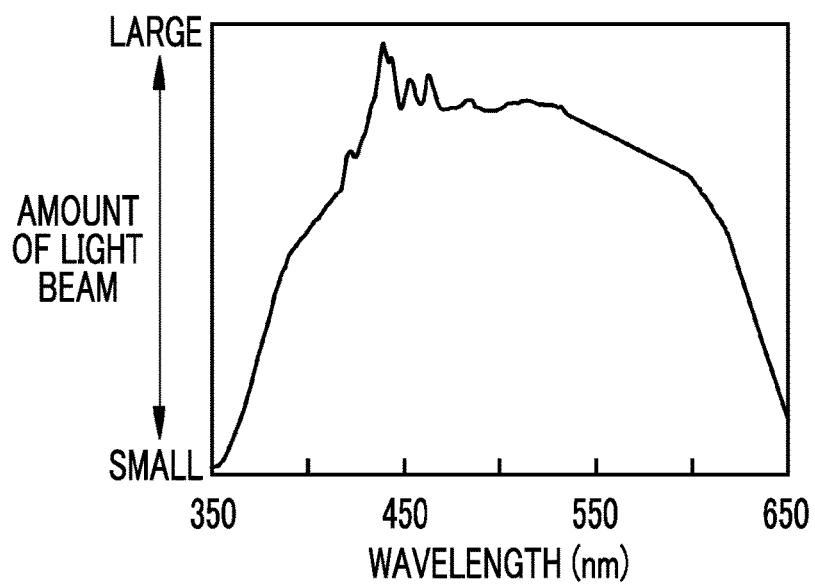
FIG. 14 is a graph showing an emission spectrum of another light source.

In the first embodiment, an example in which the subject is irradiated with the illumination light beam having a spectrum shown in FIG. 2 has been described. Meanwhile, in the second embodiment, the subject is irradiated with an illumination light beam having a spectrum shown in FIG. 15 in which a xenon lamp that emits an illumination light beam having a spectrum shown in FIG. 14 is used as a light source and a light beam having a wavelength of 425 nm or less is cut by an optical filter. In addition to the light source that emits a white light beam, such as a xenon lamp, an auxiliary light source may be provided. In this case, for example, it is preferable to provide an auxiliary light source that emits a light beam in a specific wavelength range specialized for acquiring specific biological information, such as a case where the first LED and/or the second LED described in the first embodiment is provided.

Figure 16:
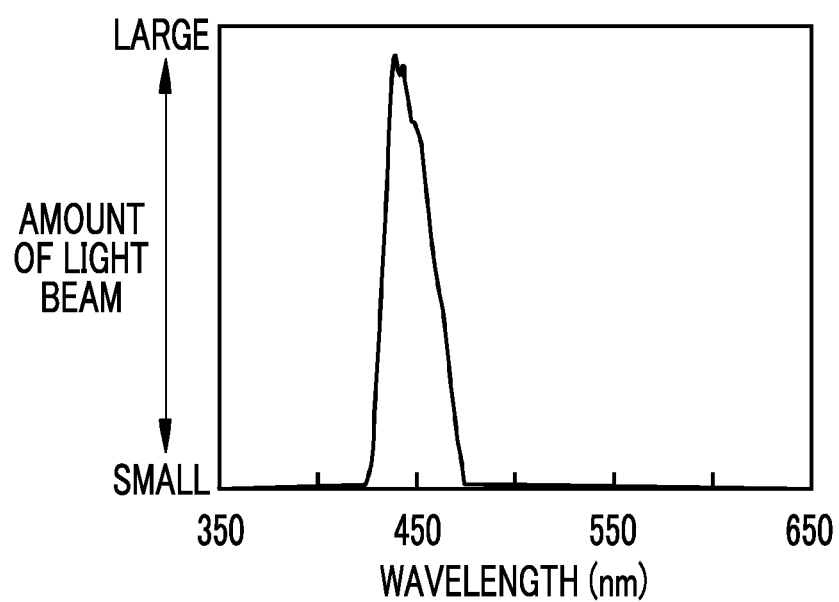
FIG. 16 is a graph showing a spectrum of a first blue light beam.
Figure 18:
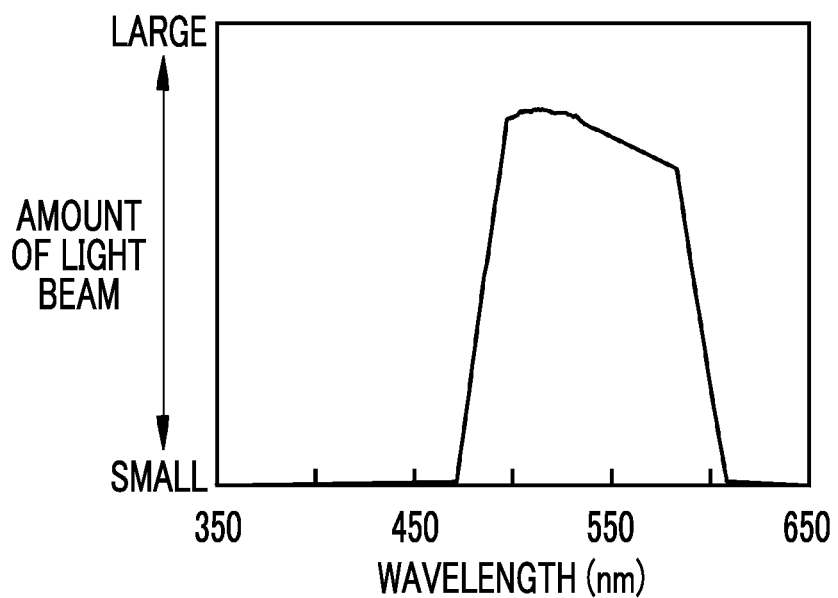
FIG. 18 is a graph showing a spectrum of a green light beam.
Figure 19:
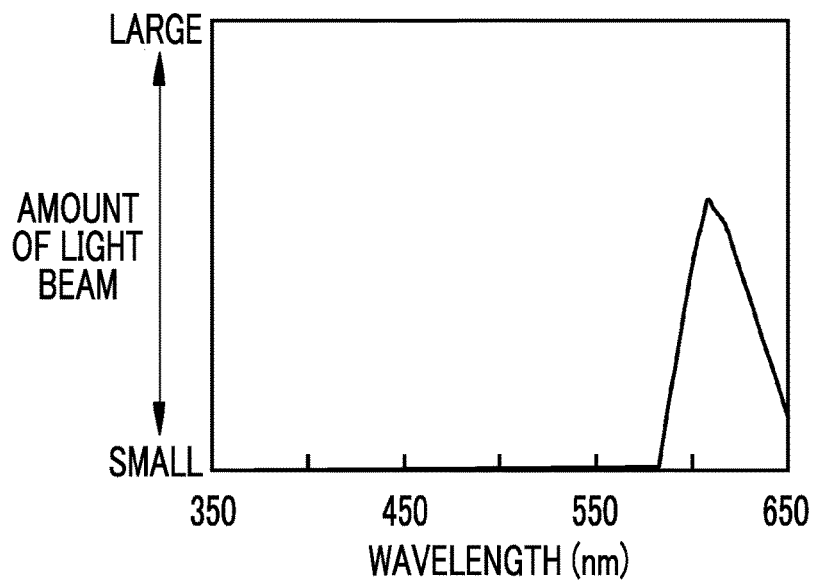
FIG. 19 is a graph showing a spectrum of a red light beam.

In the second embodiment, the first blue light beam having a spectrum shown in FIG. 16, which is reflected by the dichroic mirror 31 (see FIGS. 4 and 5), is incident on the CMOS sensor 41 (see FIG. 4). Further, the second blue light beam having a spectrum shown in FIG. 17, which is reflected by the dichroic mirror 32 (see FIGS. 4 and 6), is incident on the CMOS sensor 42 (see FIG. 4). Furthermore, the green light beam having a spectrum shown in FIG. 18, which is reflected by the dichroic mirror 33 (see FIGS. 4 and 7), is incident on the CMOS sensor 43 (see FIG. 4), and the red light beam having a spectrum shown in FIG. 19, which is transmitted through the dichroic mirror 33, is incident on the CMOS sensor 44 (see FIG. 4).

Figure 15:
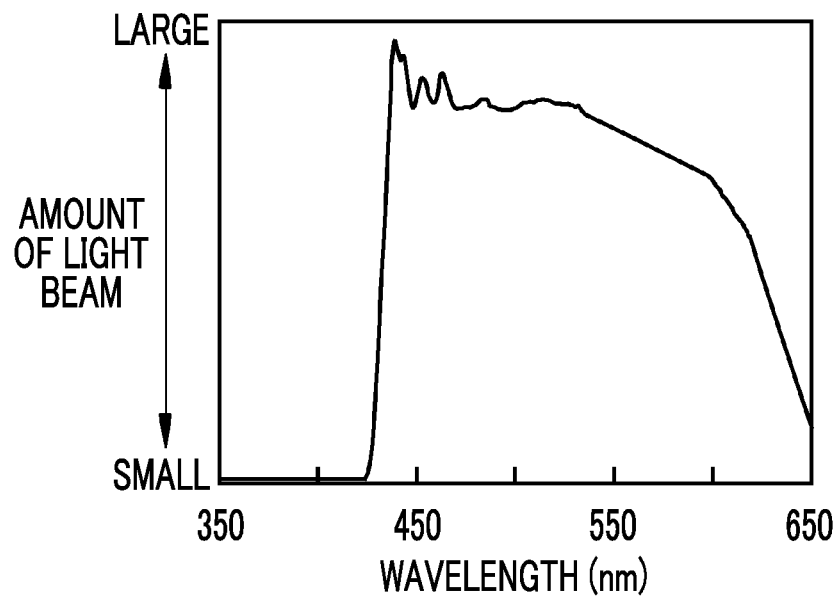
FIG. 15 is a graph showing a spectrum of an illumination light beam.
Figure 17:
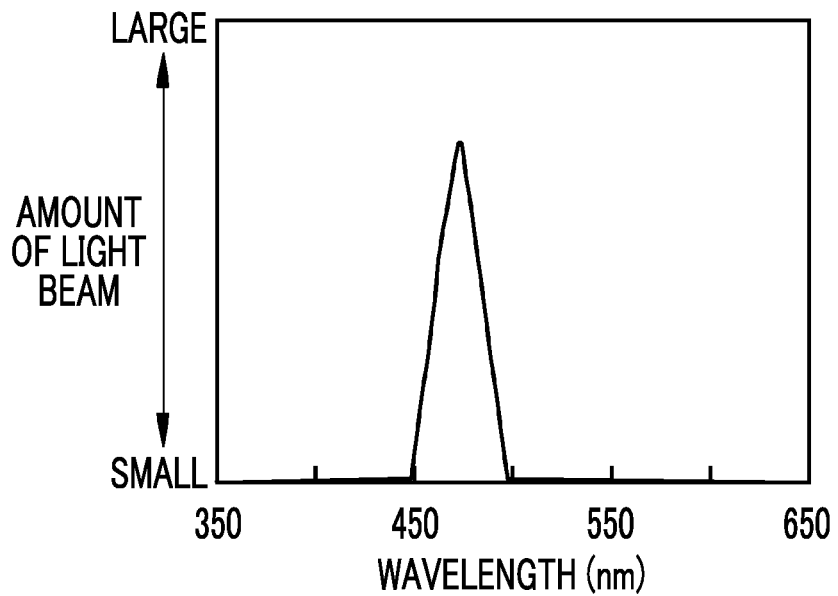
FIG. 17 is a graph showing a spectrum of a second blue light beam.

In the second embodiment, the second blue light beam also decreases as in the first embodiment (see FIGS. 15 and 17). Therefore, in the second embodiment, the control unit 59 makes the exposure time T2 of the CMOS sensor 42 longer than each of the exposure times T1, T3, and T4 of the CMOS sensors 41, 43, and 44 (see FIG. 13). By doing so, as in the first embodiment, the biological information can be acquired with higher accuracy.

In the first and second embodiments, an example in which the amount of the second blue light beam among the first blue light beam and the second blue light beam decreases has been described, but the amount of the first blue light beam may decrease depending on the feature and the like of the dichroic mirror used, in some cases. In such a case, the exposure time of the image pickup element that performs image pickup of the first blue light beam (in the first and second embodiments, the exposure time T1 of the CMOS sensor 41) may be made longer than each of the exposure times (in the first and second embodiments, the exposure times T2, T3, and T4 of the CMOS sensors 42, 43, and 44) of the other image pickup elements. Further, the amounts of both the first blue light beam and the second blue light beam may decrease depending on the features and the like of the dichroic mirror used, in some cases. In such a case, the exposure time T1 may be made longer than each of the exposure times T3 and T4, and the exposure time T2 may be made longer than each of the exposure times T3 and T4. Of course, since the exposure times T1, T2, T3, and T4 can be set independently, each exposure time may be controlled so as to satisfy, for example, "T1>T2>T3=T4".

Figure 20:
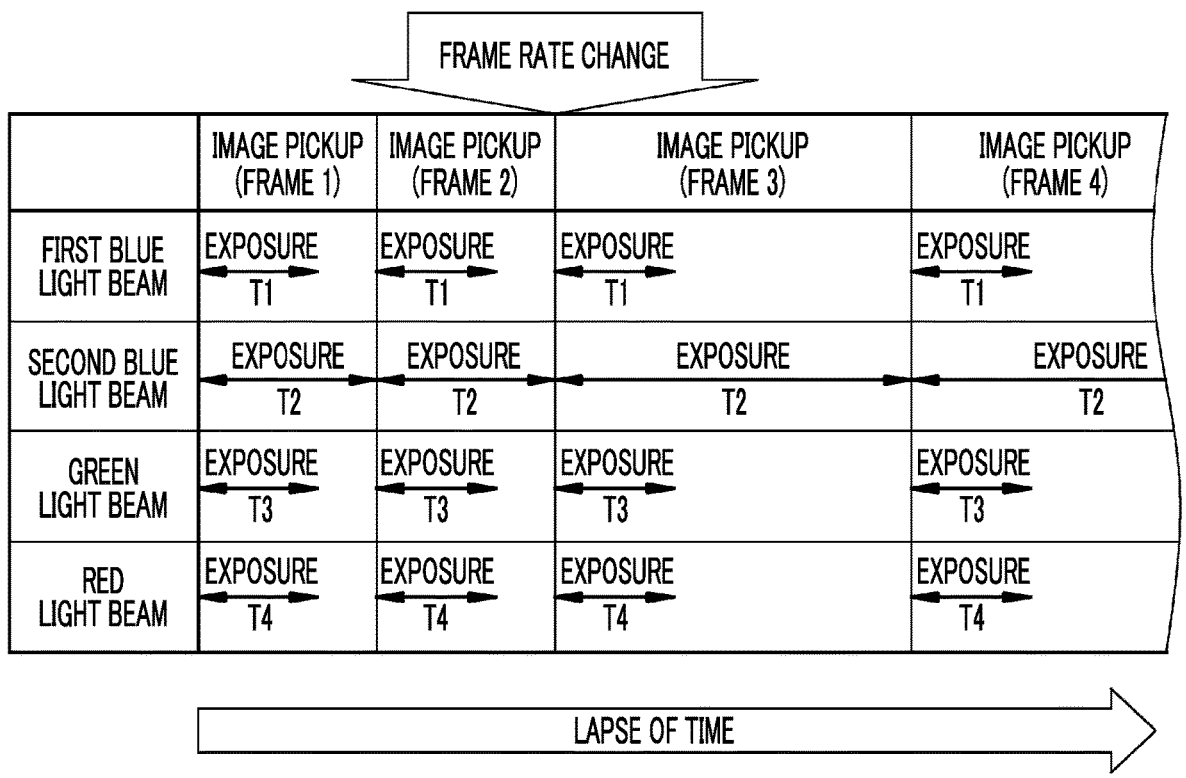
FIG. 20 is an explanatory diagram showing an example in which a frame rate is changed.

Furthermore, depending on the features and the like of the dichroic mirror used, a large amount of the first blue light beam and/or the second blue light beam may decrease, and it may be difficult to say that the exposure time is sufficient even in a case where the exposure time is made maximum within the range of the preset frame rate (all the CMOS sensors 41, 42, 43, and 44 have the common frame rate and in the first and second embodiments, the frame rate thereof is 60 fps (1/60 seconds per frame)), in some cases. In such a case, as shown in FIG. 20, the frame rate may be changed so that the exposure time can be lengthened. In this case, the frame rate may be set longer than the maximum exposure time among the exposure times of the CMOS sensors 41, 42, 43, and 44. For example, in a case where the maximum exposure time among the exposure times of the CMOS sensors 41, 42, 43, and 44 is 1/30 seconds, the frame rate may be changed to 30 fps or less. The frame rate may be changed by the control unit 59. Further, in a case where the frame rate is changed in this way, it is preferable to make the control unit 59 function as a notification unit, and for example, display the change on the monitor 18 or the like to inform (notify) the user.

Third Embodiment

In the first and second embodiments, the reflected light beam from the subject is separated into four light beams of the first blue light beam, which is a light beam in a wavelength range including a wavelength of 445 nm, the second blue light beam, which is a light beam in a wavelength range including a wavelength of 473 nm, the green light beam, and the red light beam. Meanwhile, in the third embodiment, the reflected light beam from the subject is separated into a blue light beam, a green light beam, which is a light beam in a wavelength range including a wavelength of 540 nm, a first red light beam, which is a light beam in a wavelength range (first wavelength range) including a wavelength of 600 nm (first wavelength), and a second red light beam, which is a light beam in a wavelength range (second wavelength range) including a wavelength of 630 nm (second wavelength). As described above, in the third embodiment, among the separated light beams, the first red light beam and the second red light beam are light beams in wavelength ranges close to each other (the wavelength difference between the first wavelength and the second wavelength is 30 nm or less). The red light beam (the first red light beam, the second red light beam, and the like) has a wavelength longer than that of the blue light beam (the first blue light beam, the second blue light beam, and the like), and has a property that the red light beam reaches the deeper side than the blue light beam (deeper part of the subject). That is, the blue light beam is suitable for acquiring biological information on the surface part of the subject, whereas the red light beam is suitable for acquiring biological information on the deep part of the subject.

Figure 21:
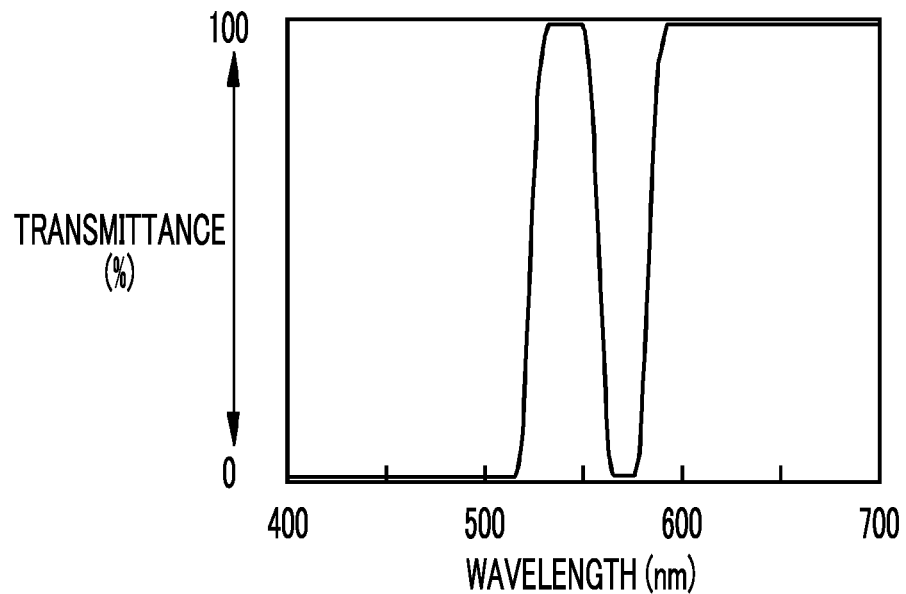
FIG. 21 is a characteristic diagram of an optical filter.

In the third embodiment, a xenon lamp that emits an illumination light beam having the same spectrum as in the second embodiment is used as a light source (see FIG. 14). Further, in the third embodiment, the subject is irradiated with an illumination light beam having a spectrum shown in FIG. 22 by using an optical filter having a relationship shown in FIG. 21 between the wavelength and the transmittance.

Further, in the third embodiment, a dichroic mirror having features that the reflectivity and the transmittance at a wavelength of 469 nm are 100% and 0%, respectively, the reflectivity and the transmittance at a wavelength of 494 nm are 0% and 100%, respectively, and in a wavelength range of 469 nm to 494 nm, the reflectivity decreases in inverse proportion to the wavelength and the transmittance increases in proportion to the wavelength, is used as the dichroic mirror 31 (see FIG. 4). As a result, a light beam having a wavelength of less than 494 nm is incident on the CMOS sensor 41 as the blue light beam. In the third embodiment, since the illumination light beam corresponding to the blue light beam is cut by the optical filter (see FIGS. 21 and 22), there is no light beam incident on the CMOS sensor 41. However, for example, the optical filter may be removed or the feature thereof may be changed to make the blue light beam incident on the CMOS sensor 41. That is, biological information may be acquired using not only the green light beam, the first red light beam, and the second red light beam, which will be described later, but also the blue light beam.

Figure 23:
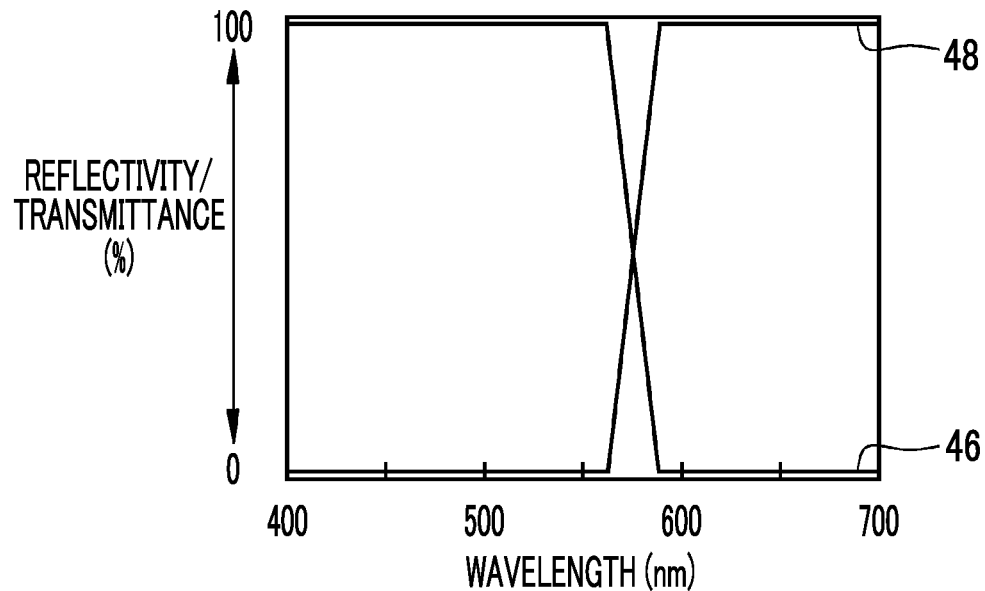
FIG. 23 is a characteristic diagram of the dichroic mirror.
Figure 24:
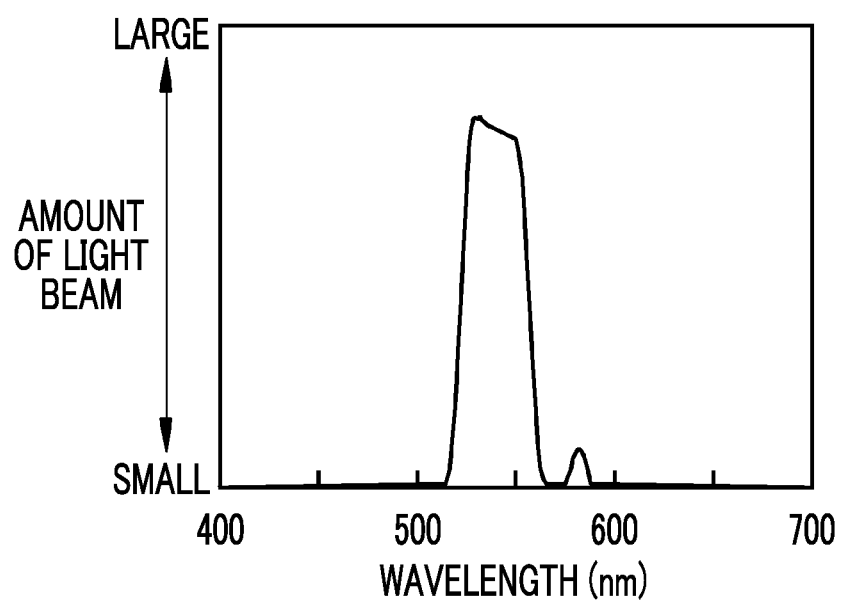
FIG. 24 is a graph showing a spectrum of a green light beam.

The light beams (the green light beam, the first red light beam, and the second red light beam) transmitted through the dichroic mirror 31 are incident on the dichroic mirror 32 (see FIG. 4). As shown in FIG. 23, in the third embodiment, a dichroic mirror having features that the reflectivity and the transmittance at a wavelength of 562 nm are 100% and 0%, respectively, the reflectivity and the transmittance at a wavelength of 587 nm are 0% and 100%, respectively, and in a wavelength range of 562 nm to 587 nm, the reflectivity decreases in inverse proportion to the wavelength and the transmittance increases in proportion to the wavelength, is used as the dichroic mirror 32. As a result, as shown in FIG.

24, a light beam having a wavelength of more than 469 nm and less than 587 nm is incident on the CMOS sensor 42 as the green light beam.

Figure 25:
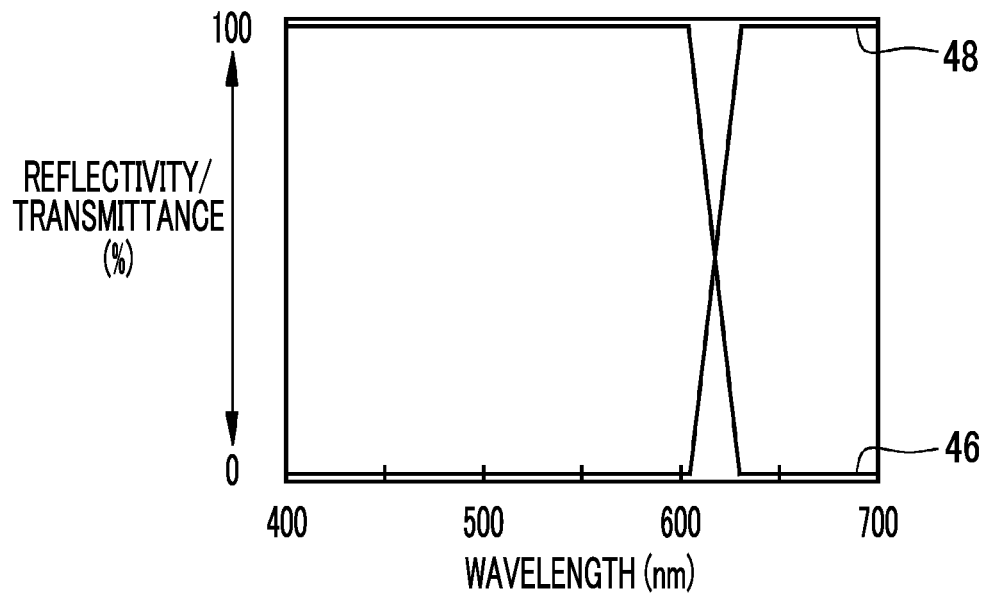
FIG. 25 is a characteristic diagram of the dichroic mirror.
Figure 26:
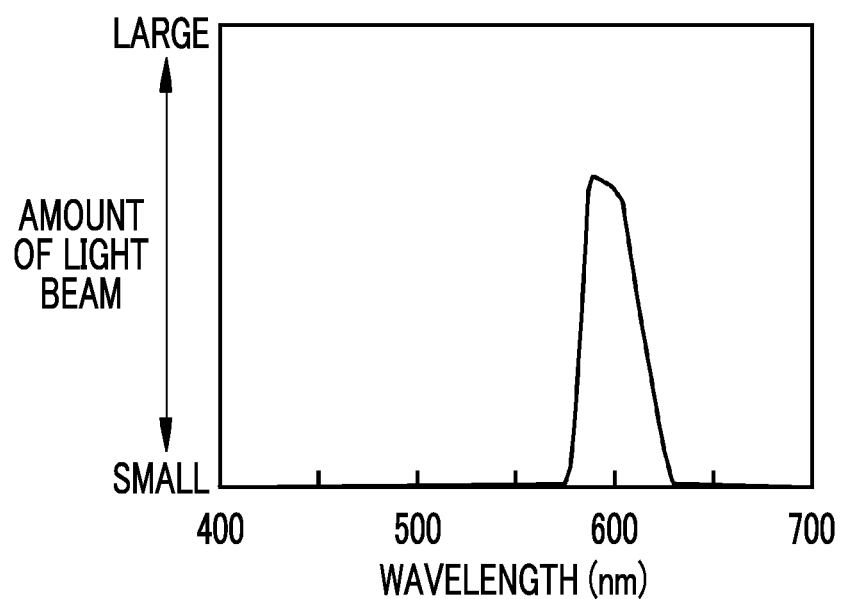
FIG. 26 is a graph showing a spectrum of a first red light beam.

The light beams (the first red light beam and the second red light beam) transmitted through the dichroic mirror 32 are incident on the dichroic mirror 33 (see FIG. 4). As shown in FIG. 25, in the third embodiment, a dichroic mirror having features that the reflectivity and the transmittance at a wavelength of 604 nm are 100% and 0%, respectively, the reflectivity and the transmittance at a wavelength of 629 nm are 0% and 100%, respectively, and in a wavelength range of 604 nm to 629 nm, the reflectivity decreases in inverse proportion to the wavelength and the transmittance increases in proportion to the wavelength, is used as the dichroic mirror 33. As a result, as shown in FIG. 26, a light beam having a wavelength of more than 562 nm and less than 629 nm is incident on the CMOS sensor 43 as the first red light beam. Further, as shown in FIG. 27, a light beam having a wavelength of more than 604 nm is incident on the CMOS sensor 43 as the second red light beam.

Figure 22:
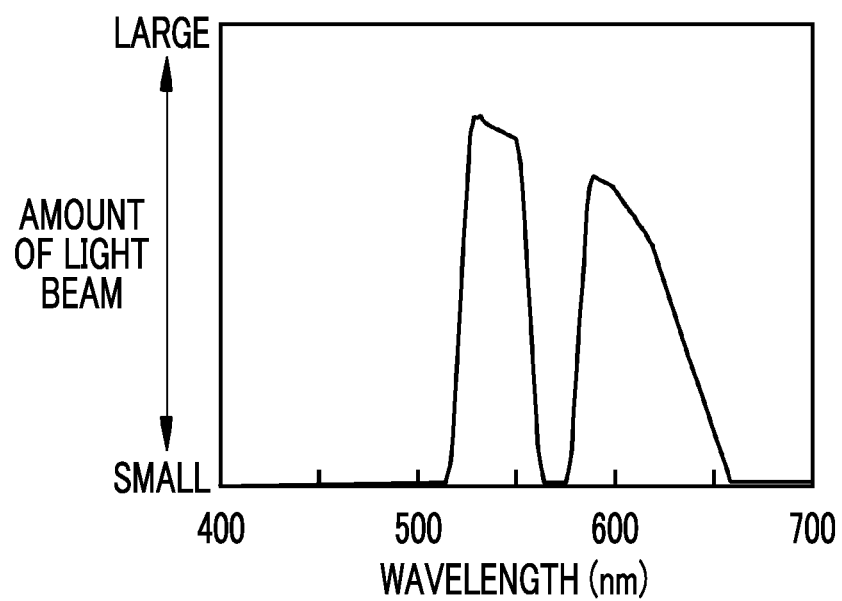
FIG. 22 is a graph showing a spectrum of an illumination light beam.
Figure 27:
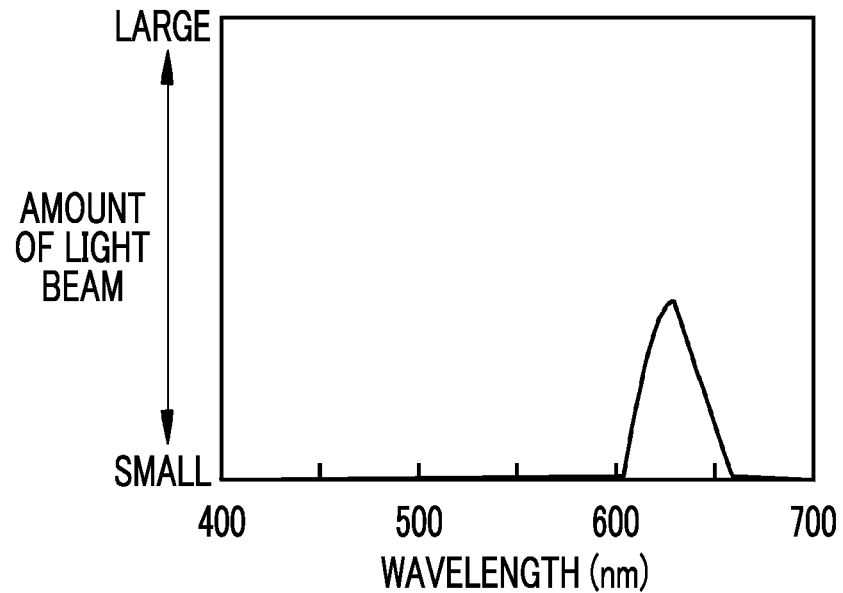
FIG. 27 is a graph showing a spectrum of a second red light beam.

In the third embodiment, the amount of the second red light beam decreases (see FIGS. 22 and 27). Therefore, in the third embodiment, the control unit 59 makes the exposure time T4 of the CMOS sensor 44 longer than each of the exposure times T1, T2, and T3 of the CMOS sensors 41, 42, and 43. By doing so, the biological information can be acquired with higher accuracy.

Figure 28:
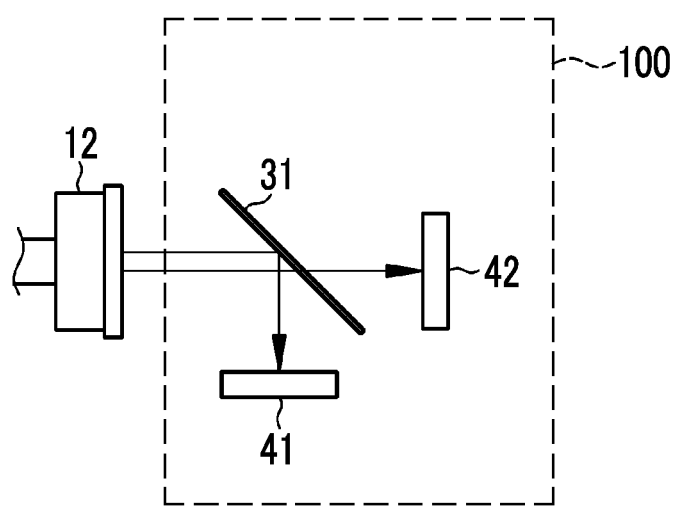
FIG. 28 is a configuration diagram of another camera head.
Figure 29:
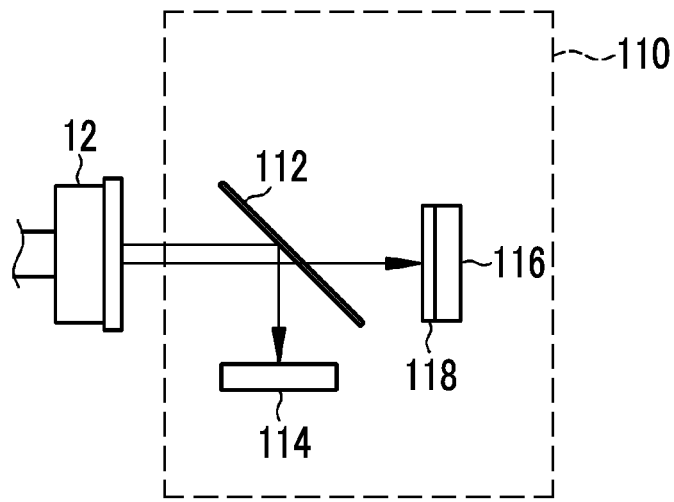
FIG. 29 is a configuration diagram of still another camera head.

In the above embodiments, an example of using the camera head provided with four image pickup elements has been described, but the present invention is not limited thereto. For example, as shown in FIG. 28 or 29, a camera head 100 or 110 provided with two image pickup elements may be used. In the description with reference to the drawings after FIG. 28, the same reference numerals are given to the same members as those in the above-described embodiments and the description thereof will not be repeated.

In FIG. 28, the camera head 100 uses a dichroic mirror having features shown in FIG. 5, as the dichroic mirror 31. In the example of FIG. 28, the light source emits the first blue light beam and the second blue light beam, the reflected light beam from the subject illuminated by the light source is separated into the first blue light beam and second blue light beam by the dichroic mirror 31, and the image of the first blue light beam is picked up by the CMOS sensor 41 and the image of the second blue light beam is picked up by the CMOS sensor 42. As in the above embodiments, the exposure time of any one of the CMOS sensors 41 or 42 (CMOS sensor in which the amount of incident light beam decreases) may be lengthened even in a case where such a camera head 100 is used.

On the other hand, in FIG. 29, the camera head 110 comprises a spectral element 112, and image pickup elements 114 and 116. The spectral element 112 is provided so as to separate a light beam in a specific wavelength range of the reflected light beam from the subject, and is, for example, a dichroic mirror that reflects the light beam in the specific wavelength range or a half mirror that reflects a part of the light beam in the specific wavelength range. The image pickup elements 114 and 116 are CMOS sensors, CCD sensors, or the like, and the image pickup element 114 is a monochrome sensor without a color filter, that is, the same sensor as the CMOS sensors 41, 42, 43, and 44 described above. On the other hand, the image pickup element 116 comprises a color filter 118. As the color filter 118, for example, a primary color filter may be used. The primary color filter is provided with a blue color filter at a position corresponding to the B pixel (blue pixel), a green color filter at a position corresponding to the G pixel (green pixel), and a red color filter at a position corresponding to the R pixel (red pixel) of the image pickup element 116. In this way, the color filter 118 is provided, so that three types of images of a B image (blue image), a G image (green image), and an R image (red image) can be picked up at the same time with one image pickup using one image pickup element 116. Of course, as the color filter 118, a complementary color filter including three color filters of yellow (Y), magenta (M), and cyan (C) may be used. As in the above embodiments, the exposure time of any one of the image pickup elements 114 or 116 (image pickup element in which the amount of incident light beam decreases) may be lengthened even in a case where such a camera head 110 is used.

Although the oxygen saturation is calculated in the above embodiments and the like, the present invention is also useful to generate, for example, an image representing other biological information (for example, an image of blood volume or a blood vessel at a specific depth). In a case where other biological information is explicitly calculated, the oxygen saturation calculation unit 70 is made a biological information calculation unit. Further, in a case where an image representing other biological information, as a result, is generated, the oxygen saturation calculation unit 70 may be made an arithmetic operation unit that performs a necessary arithmetic operation by using the signal values and/or the ratio of the signal values of the images, in order to generate the image.

Further, in the above embodiments and the like, an example in which all the image pickup elements perform image pickup at a common frame rate has been described, but the present invention is not limited thereto. The frame rates may be made different for each image pickup element.

Figure 30:
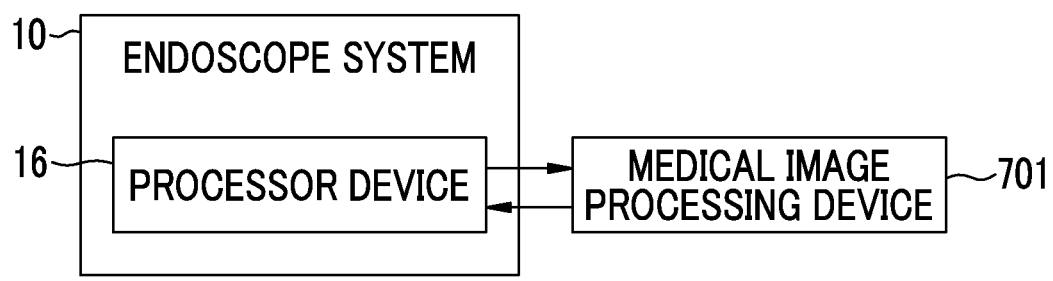
FIG. 30 is an explanatory diagram showing a relationship between another endoscope system and an image processing device.
Figure 31:
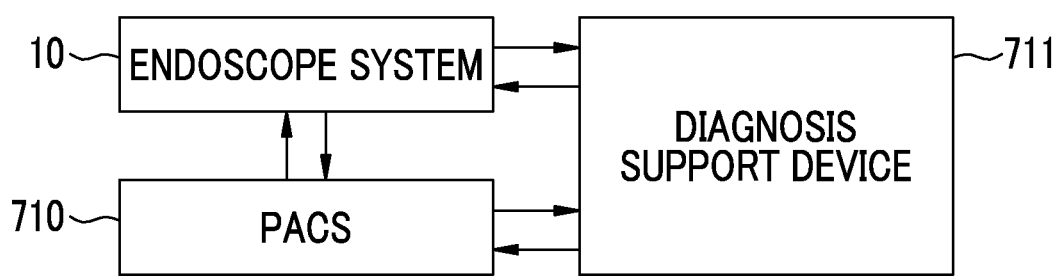
FIG. 31 is an explanatory diagram showing a relationship between still another endoscope system and PACS, and a diagnosis support device.
Figure 32:
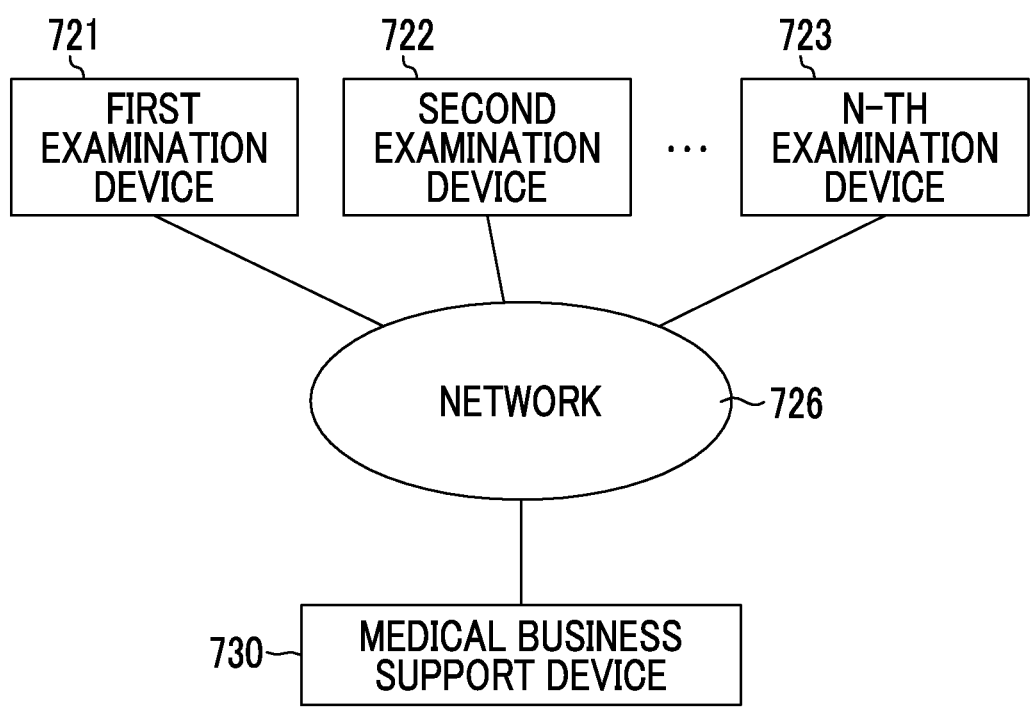
FIG. 32 is an explanatory diagram showing a relationship between various examination devices and a medical business support device.

In addition, as shown in FIG. 30, a part or all of the image processing unit 61 and/or the control unit 59 of the endoscope system 10 may be provided in, for example, a medical image processing device 701 that associates with the endoscope system 10 through the communication with the processor device 16. Further, as shown in FIG. 31, a part or all of the image processing unit 61 and/or the control unit 59 of the endoscope system 10 may be provided in, for example, a diagnosis support device 711 that acquires the image picked up by the endoscope 12 directly from the endoscope system 10 or indirectly from picture archiving and communication systems (PACS) 710. Further, as shown in FIG. 32, a part or all of the image processing unit 61 and/or the control unit 59 of the endoscope system 10 may be provided in a medical business support device 730 that is connected to various examination devices including the endoscope system 10, such as a first examination device 721, a second examination device 722, . . . , and an N-th examination device 723 via the network 726.

EXPLANATION OF REFERENCES

10: endoscope system
12: endoscope
14: light source device
15, 100, 110: camera head
16: processor device
18: monitor
19: console
20: light source unit
22 light source control unit
24: light guide
31, 32, 33: dichroic mirror (spectral element)

41, 42, 43, 44: CMOS sensor (image pickup element)
46: line showing relationship between wavelength and reflectivity of light beam to be reflected
48: line showing relationship between wavelength and transmittance of light beam to be transmitted
51: spectrum of light beam having central wavelength of 445 nm
52: spectrum of light beam having central wavelength of 473 nm
53A, 53B: region
59: control unit (image pickup control unit)
60: image acquisition unit
61: image processing unit
66: display control unit
68: correlation storage unit
70: oxygen saturation calculation unit
112: spectral element
114, 116: image pickup element
118: color filter
701: medical image processing device
710: PACS
711: diagnosis support device
721: first examination device
722: second examination device
723: N-th examination device
726: network
730: medical business support device
T1, T2, T3, T4: exposure time

What is claimed is:

1. An endoscope system that illuminates a subject and picks up an image of a reflected light beam from the subject, the endoscope system comprising:
a spectral element that separates the reflected light beam into light beams in a plurality of wavelength ranges;
a plurality of image pickup elements on which the light beams in the plurality of wavelength ranges, which are separated by the spectral element, are incident, respectively; and
a processor that controls exposure times of the plurality of image pickup elements for each image pickup element to perform image pickup,
wherein the image pickup elements include a first image pickup element on which a light beam in a first wavelength range including a first central wavelength is incident, and a second image pickup element on which a light beam in a second wavelength range including a second central wavelength of which a wavelength difference from the first central wavelength is 30 nm or less is incident,
the exposure time of at least one of the first image pickup element or the second image pickup element is longer than the exposure time of the other image pickup element, and
there is an overlap between the first wavelength range and the second wavelength range, and the exposure time of the image pickup element, on which the light beam in the wavelength range that is attenuated by the spectral element is incident, is longer than the exposure time of the other image pickup element.

2. The endoscope system according to claim 1,
wherein a first blue light beam as the light beam in the first wavelength range is incident on the first image pickup element, and a first blue image is picked up by the first image pickup element, and
a second blue light beam as the light beam in the second wavelength range is incident on the second image pickup element, and a second blue image is picked up by the second image pickup element.

3. The endoscope system according to claim 2,
wherein the first central wavelength is 445 nm and the second central wavelength is 473 nm.

4. The endoscope system according to claim 2,
wherein the processor calculates oxygen saturation using the first blue image and the second blue image.

5. The endoscope system according to claim 1,
wherein a first red light beam as the light beam in the first wavelength range is incident on the first image pickup element, and a first red image is picked up by the first image pickup element, and
a second red light beam as the light beam in the second wavelength range is incident on the second image pickup element, and a second red image is picked up by the second image pickup element.

6. The endoscope system according to claim 5,
wherein the first central wavelength is 600 nm and the second central wavelength is 630 nm.

7. The endoscope system according to claim 5,
wherein the processor calculates biological information using the first red image and the second red image.

8. The endoscope system according to claim 1,
wherein a first image pickup element and a second image pickup element are provided as the image pickup elements,
the spectral element separates a light beam in a first wavelength range including a specific wavelength from the reflected light beam, and
the light beam in the first wavelength range is incident on the first image pickup element, and a remaining light beam is incident on the second image pickup element.

9. The endoscope system according to claim 1,
wherein the processor continuously performs image pickup at a common frame rate for all the image pickup elements.

10. The endoscope system according to claim 9,
wherein in a case where there is an image pickup element that performs image pickup with an exposure time longer than the frame rate, the processor changes the frame rate longer than a longest time of the exposure times for all the image pickup elements.

11. The endoscope system according to claim 10,
wherein the processor, in a case where the frame rate is changed, gives notification of the change.

* * * * *